United States Patent [19]

Shambroom

[11] Patent Number: 5,381,804

[45] Date of Patent: Jan. 17, 1995

[54] MONITOR AND METHOD FOR ACQUIRING AND PROCESSING ELECTRICAL SIGNALS RELATING TO BODILY FUNCTIONS

[75] Inventor: John R. Shambroom, Arlington, Mass.

[73] Assignee: Aspect Medical Systems, Inc., Framingham, Mass.

[21] Appl. No.: 135,801

[22] Filed: Oct. 14, 1993

Related U.S. Application Data

[62] Division of Ser. No. 961,525, Oct. 15, 1992.

[51] Int. Cl.[6] ............................................. A61B 5/0476
[52] U.S. Cl. .................................................... 128/731
[58] Field of Search ................................. 128/639–640, 128/642, 731–734, 741; 607/96, 115, 148

[56] References Cited

U.S. PATENT DOCUMENTS

| | | | |
|---|---|---|---|
| 4,331,161 | 5/1982 | Patel | 607/96 X |
| 4,399,823 | 8/1983 | Donnelly | 607/96 X |
| 4,399,824 | 8/1983 | Davidson | 607/96 X |
| 4,598,281 | 7/1986 | Maas | 128/731 X |

Primary Examiner—Angela D. Sykes
Attorney, Agent, or Firm—Hale and Dorr

[57] ABSTRACT

A monitor for receiving electrical signals from a living body includes a power supply which is located in a housing for the monitor and a separate acquisition module which acquires signals through one or more electrodes connected to a body. Both data and power are transmitted over the same means between the power supply and the acquisition modules.

5 Claims, 10 Drawing Sheets

STATP BIT 0
    0 NO VALID STATUS
    1 VALID STATUS NIBBLE PRESENT STATUS
  NIBBLE 0 (UNUSED)
    BITS 1 2 3 4
        0 0 0 0

NIBBLE 1 (ID)
    BITS 1 2 3 4
        0 0 0 1 FRONT END TYPE / REV
        ALL OTHER STATUS UNDEFINED BUT RESERVED   NIBBLE 2 (FAULT)
    BIT 1    POWER REGULATION FAULT
    BIT 2    INTERFACE FAULT
    BIT 3    REFERENCE LEAD OFF
    BIT 4    ZERO AMPLIFIERS STATE   NIBBLE 3 (STATE)   (NOTE: STATES ARE POSITIVE TRUE)
    BIT 1    IMPEDANCE CHECK STATE
    BIT 2    TEST STATE
    BIT 3    BLOCK STATE
    BIT 4    BIPOLAR / REFERENTIAL (0/1)

NIBBLE 4 (LEAD OFF 1/2)
    BIT 1    CHANNEL 1 + LEAD OFF
    BIT 2    CHANNEL 1 - LEAD OFF
    BIT 3    CHANNEL 2 + LEAD OFF
    BIT 4    CHANNEL 2 - LEAD OFF   NIBBLE 5 (LEAD OFF 3/4)
    BIT 1    CHANNEL 3 + LEAD OFF
    BIT 2    CHANNEL 3 - LEAD OFF
    BIT 3    CHANNEL 4 + LEAD OFF
    BIT 4    CHANNEL 4 - LEAD OFF   NIBBLE 6 (UNUSED)
    BITS 1 2 3 4
        0 0 0 0

NIBBLE 7 (UNUSED)
    BITS 1 2 3 4
        0 0 0 0

*FIG. 10C*

```
|<----------------------------- FRAME ----------------------------->|
 0   1   2   3   4   5   6   7   8   9   A   B   C   D   E   F
| PREAMBLE  | CTLP |  SENDSTAT   | CK- | CK+ | TST | B/R | BLK | ZRO |  (UNUSED) |
```

SEND STAT
    BIT   210
            000   DON'T SEND STATUS
            001   STATUS NIBBLE 1
            010   STATUS NIBBLE 2
            011   STATUS NIBBLE 3
            100   STATUS NIBBLE 4
            101   STATUS NIBBLE 5

CK-
    BIT   3
            0     DO NOTHING
            1     CHECK - LEAD IMPEDANCES CK+
    BIT   4
            0     DO NOTHING
            1     CHECK + LEAD IMPEDANCES TST
    BIT   5
            0     DO NOTHING
            1     PUT FRONT END INTO TEST MODE B/R
    BIT   6
            0     BIPOLAR
            1     REFERENTIAL BLK
    BIT   7
            0     DO NOTHING
            1     PUT FRONT END INTO BLOCK MODE ZRO
    BIT   8
            0     DO NOTHING
            1     ZERO AMPLIFIERS

MONITOR AND METHOD FOR ACQUIRING AND PROCESSING ELECTRICAL SIGNALS RELATING TO BODILY FUNCTIONS

This is a divisional of copending application(s) Ser. No. 07/961,525 filed on Oct. 15, 1992, now allowed.

BACKGROUND OF THE INVENTION

The present invention relates in general to bodily electrical signal monitors, and more particularly to a monitor and method for acquiring and processing EEG data in EEG monitors.

An EEG data signal is an acquired medical electrical signal representing brain activity. The EEG data signal is in the form of complex waveforms which can be broken down into a series of sine waves. The frequencies and amplitudes of each of these sine waves are analyzed to represent the bioelectrical activity of millions of neurons in the brain. During an operation, anesthetics, neuroactive drugs, ischemia or other physiological changes in the brain are monitored by examining the EEG data. Recently, bispectral analysis of EEG data has been used to derive more complete information concerning such physiological changes. However, during use of existing EEG monitors, noise may obscure or distort the original EEG data signal.

To the naked eye, an EEG data signal looks to be significantly affected by noise, and very heavy filtering is commonly used to preserve the important characteristics of the EEG data signal. In prior art systems, filtering is often not successful because of artifacts such as electrocautery which generate noise over a wide band including the band of interest in the EEG signals. It is frequently difficult or impossible to differentiate the artifact signal in the EEG band from the EEG itself. This can lead to a situation where the artifact is mistaken for an EEG, and possibly to a misdiagnosis.

Another problem often encountered with known signal gathering devices which are connected through wires or cable to a monitor is that electrode leads will often be disconnected without the monitor accounting for the missing signals. This can lead to the production of false or misleading results which could cause further medical problems.

It is therefore a principal object of the present invention to provide a monitor and method of acquiring and processing EEG data which provides improved signal quality.

Another object of the present invention is to provide a monitor for acquiring and processing EEG data that is highly impervious to electrical noise pollution in the operating room.

It is also an object of the present invention to provide a monitor for acquiring and processing EEG data that has a portable data acquisition module with very low power requirements.

SUMMARY OF THE INVENTION

The EEG monitor of the present invention utilizes a portable data acquisition module and a substantially stationary processing module. The EEG signals are acquired and converted to an oversampled stream of digital signals by a sigma-delta modulator located in the data acquisition module. The signals are then filtered by a decimation filter located in the processing module. Additional means are also provided to monitor the electrode leads to detect when the leads become unplugged.

These and other objects, features and advantages of the invention will be apparent from the following description which should be read in light of the accompanying drawings in which corresponding reference numerals refer to corresponding parts throughout the several views.

DESCRIPTION OF A PREFERRED EMBODIMENT

Figure 1:
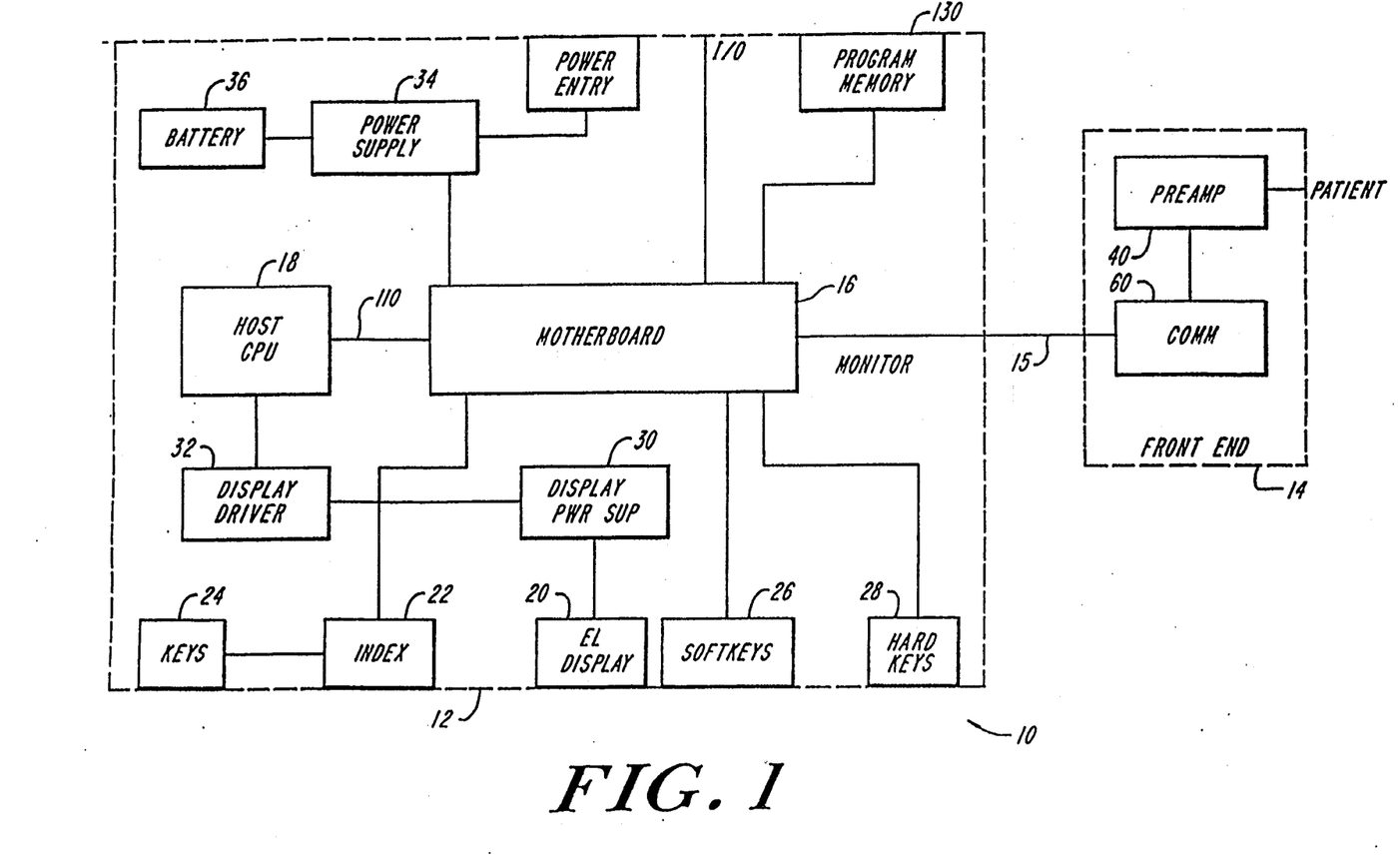
FIG. 1 is a block diagram of the EEG monitor of the present invention.

Referring to FIG. 1, the EEG monitor 10 of the present invention includes a stationary base processing module 12 and a portable data acquisition module 14. The portable data acquisition module 14 contains the circuitry required to acquire the EEG data from a patient. The data acquisition module 14 digitizes the waveforms obtained from a patient for transmission to and processing by the processing module 12. The data acquisition module 14 is connected to the processing module 12 via a thin, highly flexible cable 15. The processing module 12 processes EEG data, calculates variables, and displays waveforms and variables. All of the circuitry for acquiring and digitizing the EEG data, however, is located in the data acquisition module 14.

Figure 2:
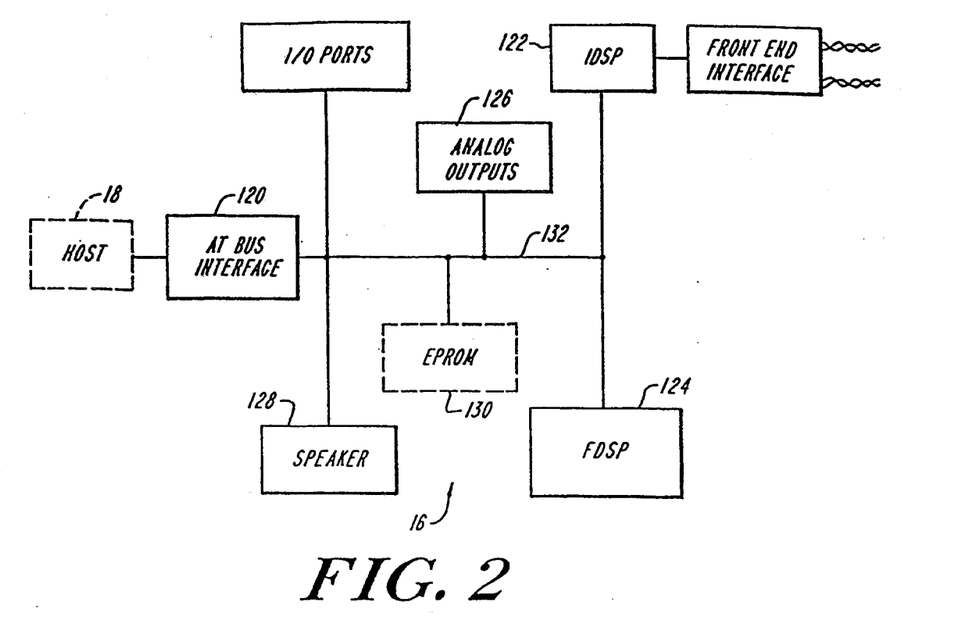
FIG. 2 is a block diagram of the circuitry of the motherboard of the EEG monitor shown in FIG. 1.

The processing module 12 includes a motherboard 16 which is shown in greater detail in FIG. 2 and which is primarily responsible for signal processing functions. A host CPU 18 is used to control the operation of the processing module 12.

In a preferred embodiment, the host CPU 18 is an 80286 16 MHz CPU, connected to 1 Mbyte non-volatile DRAM on the motherboard 16, 2 serial RS-232 ports, 1 parallel port, keyboard port, speaker port, battery backed-up real time clock, hardware watchdog timer, and a PROM 130.

The processing module 12 also includes a display 20 which in a preferred embodiment is a VGA-type display to show EEG waveforms and other information and an index display 22. The VGA display 20 is powered by display power supply 30 and controlled by display driver 32 which is connected to host CPU 118. The index display 22 contains LEDs for displaying the processed variables in solid-state seven-segment characters. In a preferred embodiment there are three full digits with decimal points, and a leading +/− display. The housing for the processing modules also includes LED indicators for ON/STANDBY, BATTERY, LOW BATTERY, and ALARM OFF.

A membrane switch panel is mounted in front of the processor module housing, and contains the switches for ON/STANDBY and ALARM OFF. Keys 24 interface to the index display board. A membrane switch panel will also preferably contain a number of soft keys 26 and hard keys 28 for functions such as FREEZE, PRINT, HELP, and START CASE.

A power supply 34 supplies power to the entire monitor and battery 36 is provided for backup purposes.

Referring to FIG. 2, the motherboard 16 of the processor module 12 will now be described. Motherboard 16 includes a bus interface 120 to the host CPU 18. In a preferred embodiment, this bus interface 108 is designed to conform with the IBM-standard AT bus specification.

An integer digital signal processor 122 connected to the bus interface 120 filters the raw EEG data and downsamples it to its final sample rate. The integer digital signal processor 122 may also detect artifacts at frequencies both in the base band and higher than the base band. In a preferred embodiment, the integer digital signal processor 122 is an Analog Devices ADSP2105 processor running at 10.245 Mhz.

Raw EEG data signals are transferred from the integer digital signal processor 122 to the host CPU 18 for display. The raw EEG waveforms are electronically displayed, as are a variety of variables which are processed from the EEG by the monitor of the present invention.

The integer digital signal processor 122 transmits raw EEG data to the floating point digital signal processor 124 at 128 words/second/channel via a serial port. The floating point digital signal processor 124 computes all of the processed variables from the EEG data, including bispectral indices if desired. In a preferred embodiment, the floating point digital signal processor 124 is a Texas Instruments TMS320C30 processor. In the preferred embodiment, the floating point digital signal processor runs at 33.33 MHz.

Four analog outputs 126 are provided to drive a chart recorder or any analog input device. A speaker 128 is used for audible alarms. The host provides the speaker tones, while the volume is set via an I/O register on the AT bus. The speaker amplifier and volume control are on the motherboard.

The operating code for the monitor is preferably located in programmable read-only memory 130 on a board that is accessible from the rear of the stationary processing module 12, allowing software changes to be made without dismantling the processing module 12. The EPROM 130 is interfaced to the AT bus 132. In the preferred embodiment, the board can accept either 1 or 2 Mbytes of PROM.

The external I/O connectors for the processing module 12 are mounted on the motherboard 16. In the preferred embodiment, the motherboard 16 occupies the full depth of the processing module 12.

Figure 3:
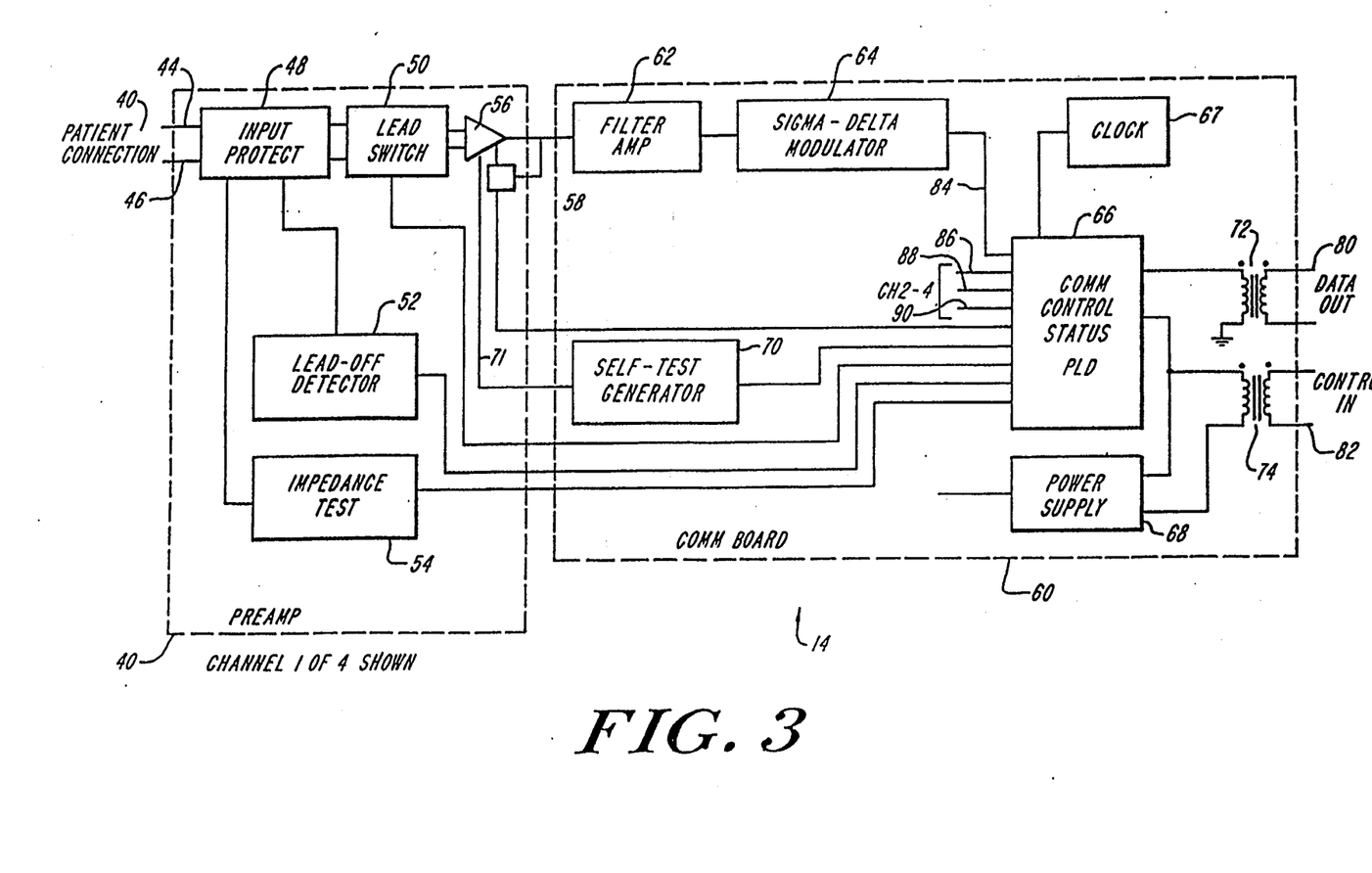
FIG. 3 is a block diagram of the circuitry of one channel of the portable data acquisition module 14 of the EEG monitor shown in FIG. 1.

Referring to FIG. 3, the circuitry for one of the four channels of the portable data acquisition module 14 will now be described. The circuitry for the other three channels of the data acquisition module 14 is substantially identical to the circuitry shown in FIG. 3.

In a preferred embodiment, data acquisition module 14 has connections 40 for ten electrodes. Eight of the electrodes are used as bipolar inputs for the four EEG data channels. The EEG data channels can be operated as either bipolar or referential, and one of the electrodes is used as a positive reference when the data channels are being operated in referential mode. The last electrode is used as an electrical ground for the patient and the portable data acquisition module 14. Two electrode input jacks 44, 46 are shown for the first data channel. In the preferred embodiment, unused inputs are shorted externally, but they could be software controlled as well.

An input protection circuit 48 protects the data acquisition module 14 from damage resulting from electric shock from low capacity sources such as people. The module 14 is designed to survive a defibrillator pulse to the patient. Input protection circuit 48 also reduces the effects from high frequency ambient noise from sources such as electrocautery and other devices found in the operating room.

For each of the four data channels there is there a montage mode switch 50, differential amplifiers 56, DC servo 58, impedance test circuit 54, and lead off detection circuits 52. There are circuits for injecting self-test voltages into the amplifier inputs. Portions of the self test circuits are on the preamp board 40 as well. The inputs to all four EEG data channels can simultaneously be zeroed on command from the host.

Impedance testing of the electrodes is under control of the host CPU 18. This is done by injecting a current of less than 0.2 µA (per AAMI standard for ECG) into each electrode at a frequency within the normal EEG bandwidth and measuring the resulting voltages. A sinusoidal current source is switched into each electrode while a digital signal processor measures the resulting voltage. The host CPU 18 controls the electrode switching. All the positive electrode leads are tested at the same time, and then all the negative electrode leads are tested. The impedance measurement range is 0–25 Kohms. The ground electrode impedance is not measured. The impedance test results enable the EEG technician to match the impedance of the electrodes and to achieve the best noise and common mode rejection performance.

The EEG data signals are amplified by a full instrumentation amplifier 56 which has a fixed gain. Each amplifier has a DC servo 58 which removes all signals below a high pass cutoff frequency. In the event of amplifier overload, the servos 58 can be changed to a higher frequency to facilitate fast recovery. Recovery is performed under control of the host processor 18. The host sets the amplifier mode to either bipolar or referential upon a request by an operator through a control on the processing module housing. Light emitting diodes, located in the preferred embodiment, on the preamp board 40 of data acquisition module 14 indicate the mode currently in use.

The communications board 60 on portable data acquisition module 14 contains an amplifier/filter circuit 62 and a sigma-delta modulator 64 for each EEG data channel. The communications board 60 also contains interface multiplexer 66 (which in a preferred embodiment is a programmable logic device), power supply circuits 68, self-test circuit 70 for producing the test tone, and a comparator for the lead off detector 52. A crystal controlled portable data acquisition module master clock 67 drives the modulators 64 and the interface at a divided rate through the PLD 66.

Each EEG data channel is amplified by an amplifier/filter circuit 62 to the level required by the analog to digital modulator 64, as will be described in greater detail below in connection with FIG. 6. Amplifier 62 also serves as a filter to prevent aliasing by the modulator 64. The filter 24 is of the third order, and is set to a frequency well above the required EEG bandwidth. This preserves the linear phase of the signal and enables the detection of artifacts over a wide bandwidth. In a preferred embodiment, sigma-delta modulator 64 runs at 16384 Hz, and is also of third order. This permits the final decimated sample rate of 128 Hz to yield better than 14 bit signal to noise ratio performance, which is more than acceptable for the EEG.

A calibrated test signal is generated on the communications board 60 by self-test generator 70 under command from the host processor 18 on the processor module 12. The signal 71 is a 2 Hz square wave of $+/-100$ $\mu V$. It is applied to the inputs of the differential amplifiers 56, where it drives the gain ports of amplifiers 56, resulting in a test of the entire signal path except for the input jacks 44, 46, protection circuits 22 and lead switches 50.

The interface from the data acquisition module 14 to the processing module 12 is comprised of a data-out serial line 80 and a control-in serial line 82. The outputs from each of the four EEG data channels 84, 86, 88, 90 are multiplexed in interface multiplexer 66, which as described above is a programmable logic device. Status information such module identification, mode (bipolar or referential), lead off indication, and power supply faults is multiplexed with the EEG data. The status information is transmitted only on command from the processing module 12.

The output from the interface multiplexer 66 is transformer-coupled onto a balanced, twisted pair line. The transformers 72, 74 provide the required patient isolation from ground.

One twisted-pair signal, which provides the control data, also transmits power from the processing module 12 to the data acquisition module 14. The data on the control-in line 82 and the data-out line 80 is bi-phase encoded. In other embodiments, the signals may be transmitted optically or through a wireless (e.g., radio) connection.

Figure 8:
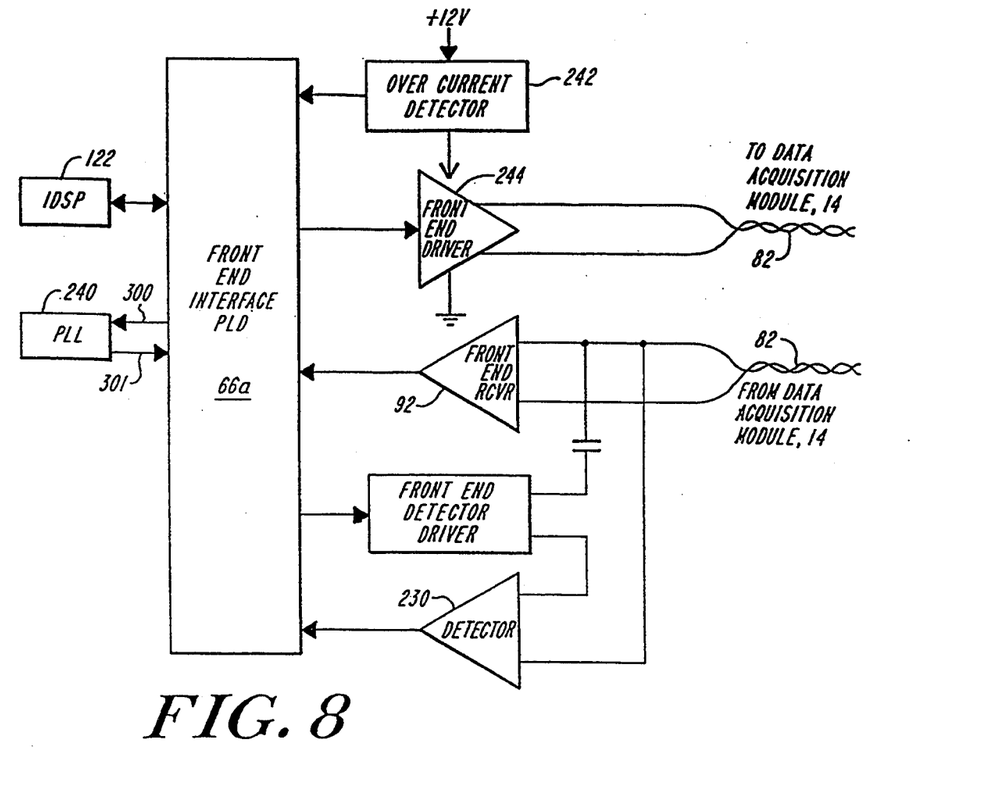
FIG. 8 is a block diagram of the front end interface of the EEG monitor shown in FIG. 1.

The control-in line is driven by the front end driver 244 (see FIG. 8). In the preferred embodiment, the drive signal is balanced, and output levels are 0 to 12 volts peak to peak. After passing through a shielded twisted pair line 82, the signals are coupled onto the communications board 60 by means of a transformer 74 (see FIG. 4). The signals are passed onto the control data receiver 116 which converts them to TTL levels before sending them to the decoder PLD 66. The communications board 60 decodes the control information coming from the processing module 12 via control-in line 82. Commands such as "auto-recover from amplifier saturation" and "conduct impedance tests" are transmitted by the host CPU 18 to the communications board 60. The control-in data rate is synchronized to the EEG data-out rate by a phase-locked loop (as described in greater detail below in FIGS. 8 and 9) in the data processing module 12, preventing interference on the EEG data signals from the command-in line.

Figure 4:
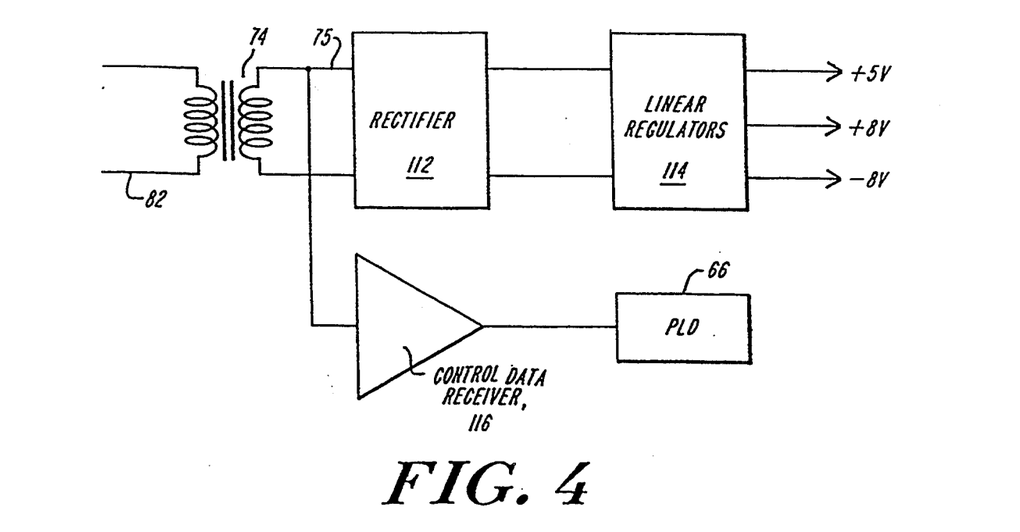
FIG. 4 is a block diagram of the data and power conversion circuitry for the data acquisition module of the EEG monitor shown in FIG. 1.

Referring to FIG. 4, the data acquisition module 14 also derives power from the control-in line 82. The transformer coupled control-in signal 75 is rectified by rectifier 112. The resulting DC signal is linearly regulated by regulators 114 to provide power to the data acquisition module 14 at the appropriate voltages.

Figure 5:
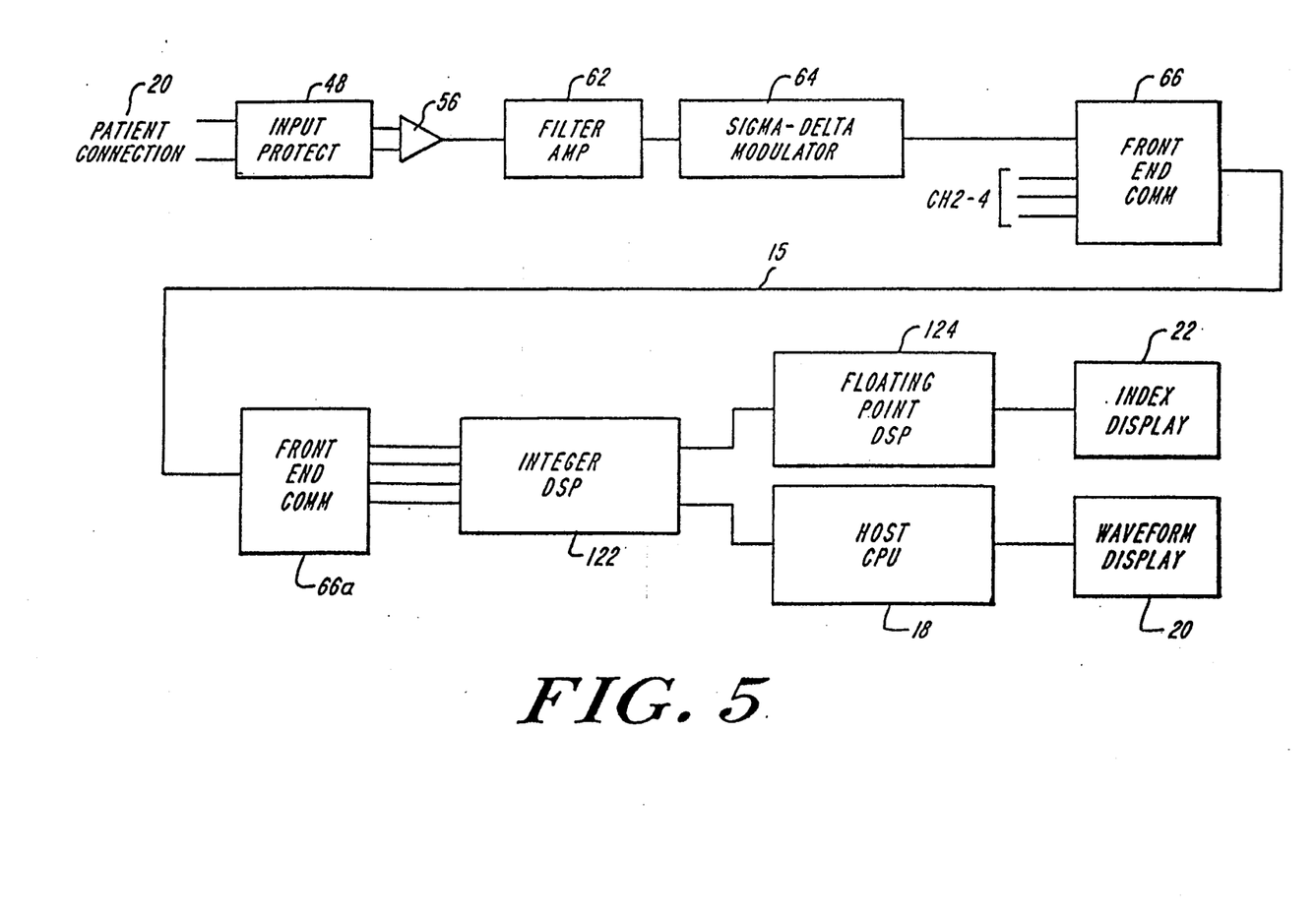
FIG. 5 is a block diagram showing the flow of EEG data signals through the EEG monitor shown in FIG. 1.
Figure 9:
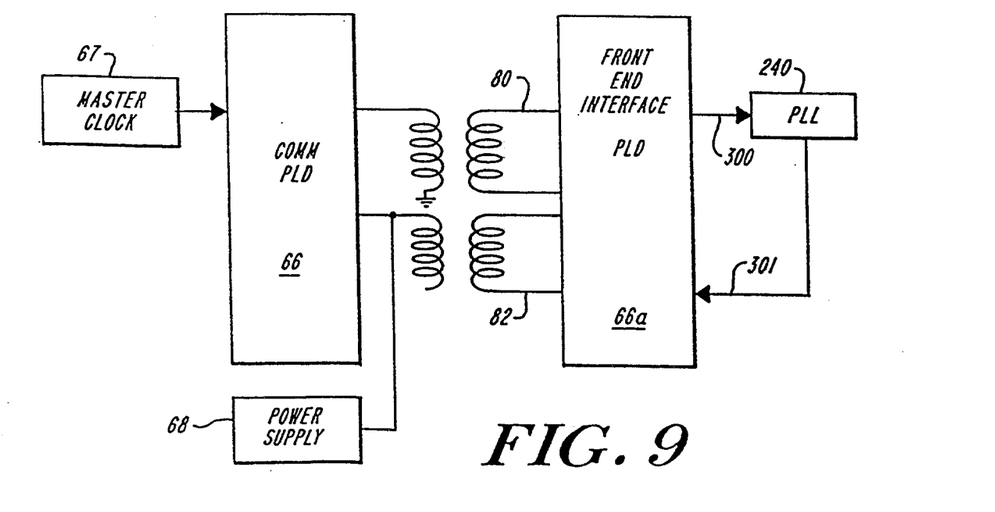
FIG. 9 is a block diagram of the relationship of the clock synchronization components of the EEG monitor shown in FIG. 1.

All of the circuits in the data acquisition module 14 are exactly synchronized to the master clock 67, which in the preferred embodiment is a crystal controlled 2.0977152 MHz clock. Referring to FIGS. 8 and 9, the master clock 67 clocks the communications PLD 66 in the data acquisition module 14. The data-out signal 80 is thus synchronous with the master clock 67. The front end interface PLD 66a recovers the synchronized clock 300 from the data-out line 80, and feeds the recovered clock 300 to the phase locked loop 240. The phase locked loop 240 generates a higher frequency clock 301 that is synchronized to the recovered clock 300, and is thus also synchronous with the master clock 67. The PLL 240 sends this clock back to the front end interface PLD 66a, which uses it to clock the control-in line 82 to the data acquisition module 14. The data acquisition module 14 uses this synchronized signal to decode control information and generate power. In this way, all of the circuits in the data acquisition module 14 operate at frequencies that are exactly synchronized with the master clock 67. This provides the advantage that signals coming back into the data acquisition module 14 will not cause interference by mixing with the clock signals already in the module 14, disturbing the sensitive EEG acquisition circuits, Before describing the specific components of the present invention, the data signal flow through the EEG monitor 10 will now be described in connection with FIG. 5. In a preferred embodiment, four channels of EEG data are processed by the monitor 10, although in other embodiments more channels or fewer channels may be processed. FIG. 5 shows the data flow for one channel of data and the data flow for the other three channels is substantially identical. EEG data signals for one channel are acquired via patient connection 20. The other three patient connections, identical to patient connection 20, are not shown in FIG. 5. The EEG data signals pass through input protection circuit 48 in the data acquisition module 14. There are four input protection circuits, although only one is shown. Each channel of EEG data is differentially amplified by instrumentation amplifiers 56, and further amplified and filtered to remove DC and high frequency components by four separate amplifier/filter circuits 62. The EEG data signals for each channel are then digitized by one bit sigma-delta analog-to-digital modulators 64 connected to each channel.

The outputs from all four modulators are multiplexed by multiplexer 66 for transfer from the data acquisition module 14 over cable 16 to the processing module 12 where they are demultiplexed by a demultiplexer 66a. After being demultiplexed, the EEG data signals are transferred to integer digital signal processor (IDSP)

122. The processor 122 digitally filters the signals and downsamples them before transmitting them to the host CPU 18 for display 20. The integer digital signal processor 122 concurrently filters and downsamples the signals for processing by floating point digital signal processor (FDSP) 124. The resulting processed variables are displayed by index display 22.

Figure 6:
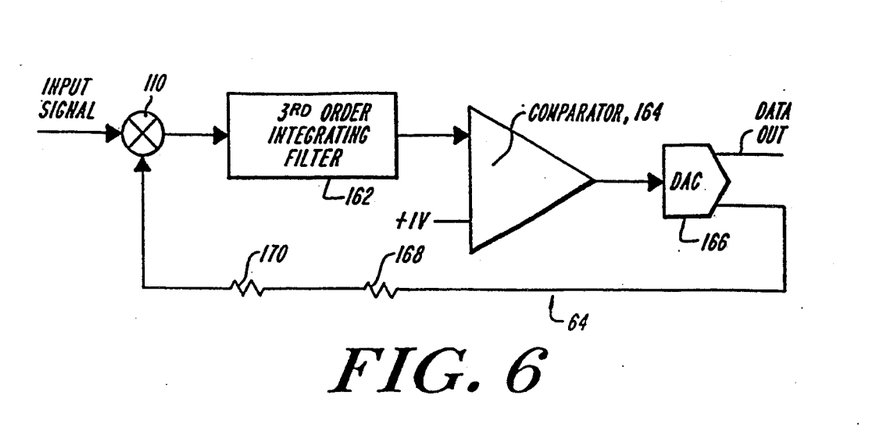
FIG. 6 is a block diagram of the sigma-delta modulator of the EEG monitor shown in FIG. 1.

Referring now to FIG. 6, the analog-to-digital conversion techniques of the present invention, which provide many advantages over prior art systems in the acquisition of the medical signals, will now be described. As indicated above, the converter of the present invention is comprised of a sigma-delta modulator 64 in the data acquisition module 14 and the digital signal processor 122 in the processing module 12. In the present invention, there are four converters, one for each data channel.

The sigma-delta modulator 64 is provided to convert the signal of interest to a digital form. Converters of any type can only approximate the signal, yielding limited resolution, signal-to-noise ratio, distortion and frequency band width. Conventional converters typically sample the signal at just above the Nyquist rate (two times the highest frequency of interest), and convert to the final required resolution and noise performance (proportional to the number of bits converted). Such converters require sample and hold circuits and complex analog filters which must filter the circuit prior to feeding them to the converter. In addition, the implementation of conventional converters usually requires accurately matched analog components. All of these elements contribute to the high cost of such converters and significantly limit the converter's performance.

The sigma-delta modulator 64 shown in FIG. 6 is an oversampling converter of the single bit sigma-delta type. A comparator 164 is used as the quantizer to determine if the signal is above or below one volt. The output of the comparator is sampled by a flip-flop 166. The output of the flip-flop is meant to be the digital representation of the analog signal. The flip-flop is also used as a one bit digital to analog converter (DAC). The output of the converter, which is the current through resistors 168, 170 is subtracted from the analog input signal by summing circuit 160 (as the inverted output of the flip-flop 166 is used for the DAC). The resulting signal is therefore the difference between the actual analog signal and the digital representation of it, i.e. the error. This error signal is integrated and fed to the comparator 164 which is acting only on the error signal in an effort to make the digital representation closely approximate the analog signal. Because the integrating filter 162 has very high gain at low frequency, it tends to minimize error at low frequencies. The output of the modulator, therefore, is a fast signal (oversampled) that contains very small errors for low frequency waveforms, but very large errors for higher frequency waveforms. The resulting converter is inherently linear (little or no distortion) because the quantizer is a single comparator, and therefore no circuits require matching.

In a processing module 12, the one bit data stream from the modulator is received at 16,384 samples per second and contains frequencies up to half that number in Hz. The decimator or integer digital signal processor 122 filters out (downsamples) the frequencies above 50 Hz and reduces the sample rate to 128 samples per second. In the preferred embodiment it does this in three steps, which is the most computationally efficient method. The first stage filters to 100 Hz and outputs at 2,048 samples per second. The second stage filters to 100 Hz, but outputs at 256 samples per second. The final stage filters to 50 Hz and outputs at 128 samples per second.

There are several distinct advantages to separating the modulator 64 from the decimator 122. The main advantage is that all of the sensitive analog electronics reside together in a small module (the data acquisition module 14) away from the noisy environment of the processing module 12, tremendously improving the quality of the digitized signal. Secondly, because the converters output only a single bit sample, each at a high rate, and utilize biphase encoding (as described below) which enables the converters to be self-clocking with each frame having one bit from each channel the interface between the two modules 12 and 14 is very robust. If the interface were hit by very severe interference from a source such as electrocautery in the operating room, only a single sample of one bit at a very high rate would be lost. Because the digital signal processor 122 is essentially averaging the digitized signal, any loss of data on the interface is averaged out and is barely noticeable in the final output.

Known conversion techniques output 12, 14, or 16 bit data samples at a lower rate than does the monitor of the present invention. In known systems, if there is a fault in the interface, the entire sample must be discarded, resulting in a very significant aberration or artifact on the output, which might be displayed as a sudden sharp jump of the signal. In the monitor of the present invention, at most a very small wiggle would appear in the display.

Another advantage of separating the modulator 64 from the decimator 122 is that the electronics in the portable data acquisition module 14 can be connected to a very low power source. In the present invention, about one watt is required to digitize four channels of EEG data signals. It is therefore possible to have a battery-powered data acquisition module that transmits its data optically.

The use of sigma-delta analog-to-digital conversion techniques also allows for improved artifact detection. Because the sigma-delta modulators 64 highly oversample the incoming signal, the signal can be viewed at a greater bandwidth. At higher bandwidths, however, the signal-to-noise ratio is much poorer. Significant artifacts may be characterized by either high slew rates coming in or by a large jump in the noise level over a wide bandwidth. In the present invention, EEG signals are monitored at up to a 1 KHz bandwidth. One technique for detecting an artifact is to monitor the total power in the 0.25 Hz to 1 KHz bandwidth and to look for a significant jump in the level. Another technique is to look for signals that have a very high slew rate. The bandwidth of the system of the present invention allows slew rates of over 60 volts/second to be detected. In a conventional system which is not oversampled, it is only possible to digitize slew rates of up to 0.6 volts/second. Interference from sources such as electrocautery, saws, and laser, frequently cause spiking on the waveform. When the signals are heavily filtered before being acquired, these spikes are blunted, and difficult to detect. In the present invention, digital signal processing is used to examine the wide-band signals prior to filtering and displaying, and to look for the presence of these spikes. The spikes, however, should only be detected and not be filtered out so that the presence of the artifact in the data is flagged. Since EEG data is very noise-like, it is actually dangerous to filter too much as it would not be clear which data is artifact and which is EEG.

Figure 7:
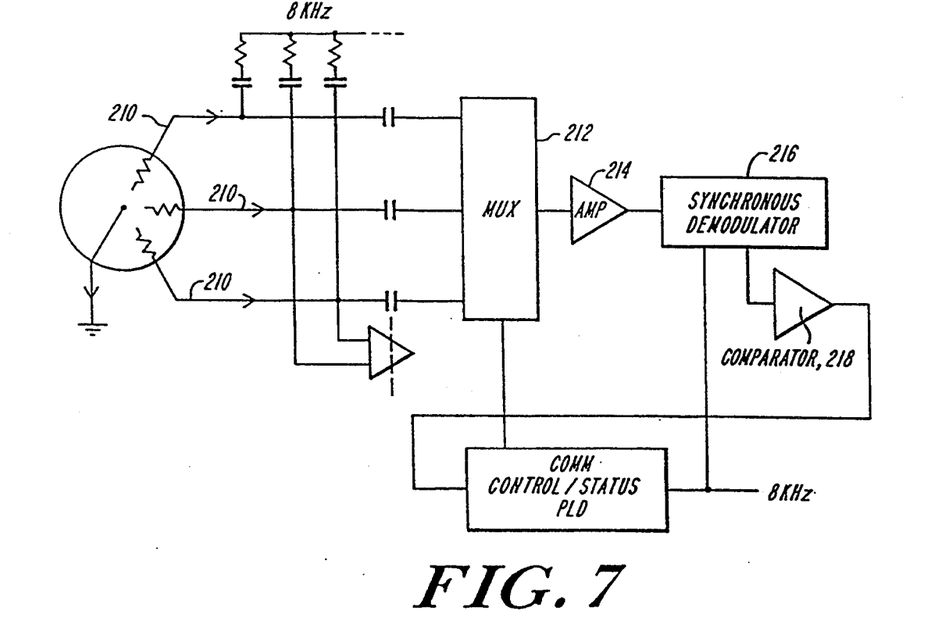
FIG. 7 is a block diagram of the circuitry for detecting that the leads are off the head utilized by the EEG monitor shown in FIG. 1.

A "leads-off" detection circuit 52, shown in greater detail in FIG. 7, in the portable data acquisition module 14 constantly monitors all of the data input leads to determine whether an electrode lead has become disconnected from the patient.

The data acquisition module 14 constantly monitors the electrode leads 210 for disconnection without control from the host. The "leads-off" detection circuit 52 constantly monitors all of the leads connected to the patient except for the ground lead by supplying a tiny current of less than 1 $\mu$A to all leads 210 simultaneously. The current is applied at exactly one-half the analog-to-digital sampling rate, which in the preferred embodiment is approximately 8 KHz. The current is exactly synchronized to the sampling rate, which ensures that the signals fall directly into a null in the analog-to-digital converter's transfer function. The disconnection monitoring method therefore adds no spurious signal or excess noise to the EEG signal. The currents introduced into the leads 210 induce a voltage that is proportional to the impedance of the lead at 8 KHz. The lead impedance at 8 KHz is typically approximately one-tenth of the lead impedance in the preferred embodiment's base band of 0–100 Hz. The circuits are calibrated such that electrode lead impedances of greater than 5 Kohms at 8 KHz corresponding to approximately 50 Kohms at 0–100 Hz is the threshold for indicating a "lead-off".

The "lead-off" detection circuit 52 AC-couples the small 8 KHz voltage from each lead into a multiplexer 212 attached to a high gain amplifier 214. The multiplexer 212 switches from lead to lead looking at only a single lead at a time with respect to the data acquisition module 14 ground which is attached to the patient ground. The output of the high gain amplifier 214 drives a synchronous demodulator 216 that is synchronized to the incoming 8 KHz signal. The demodulator 216 rectifies the 8 KHz incoming square wave signal (which is on top of the EEG data on a combined signal) at exactly 8 KHz by determining the amplitude of the 8 KHz signal thereby in effect determining the peak-to-peak voltage by stripping out the square wave signal in order to output only a DC signal proportional to the peak-to-peak voltage of the 8 KHz portion of the signal which is proportional to the electrode impedance on the head. The output of the amplifier feeds a comparator 218 located on the COMM Board 60 which is preset to a voltage which indicates an unacceptable "lead-off" condition for voltages corresponding to electrode lead impedances of greater than 5 Kohms. The interface circuit latches the output of the comparator at the end of the sampling interval for each particular lead. In the preferred embodiment, the sampling interval is ½ second per lead and the circuits therefore can scan all nine leads every five seconds.

The portable data acquisition module 14 can be disconnected for transportation with the patient, which frequently results in an open ended cable dangling in the operating room. Referring to FIG. 8, to make this a safe condition, the interface drivers (such as driver 244) are shut off by the host CPU which shuts off the drivers when it stops receiving data. In addition, an overcurrent detector 242 in the processing module 12 automatically shuts off power to the data acquisition module 14.

To detect when the data acquisition module 14 has been reconnected without being powered-up, a short duration voltage pulse of less than 100 $\mu$Sec (in the preferred embodiment, 5.7 $\mu$Sec) is applied by the front end interface to the data acquisition module interface 14. When the data acquisition module 14 is reconnected, the pulse appears across the transformer 74, and droops because of the primary inductance. The amount of droop is well defined, and is measured after a fixed time period by comparator 230 in the processing module 12. Therefore, the method to detect when the front end has been reconnected needs no extra wires, and will not incorrectly conclude that the data acquisition module 14 has been reconnected when there is a fault, such as a direct short or a weak short caused by excess saline solution, at the end of the cable.

The control-in 82 and data-out 80 lines are individually shielded twisted pairs. In the preferred embodiment, the EEG data from the data acquisition module 14 is being received at 16,384 bits/second/channel. The interface runs at a top speed of 262,144 Hz.

The power to the interface 15 is under software control. In addition, an overcurrent detector 242 monitors the current that is supplied to the data acquisition module 14. If the current exceeds the expected value, the power to the data acquisition module 14 is shut off by the hardware in the front end driver 244 and the integer digital signal processor 122 is notified via a bit set in a status register.

Figure 10A:
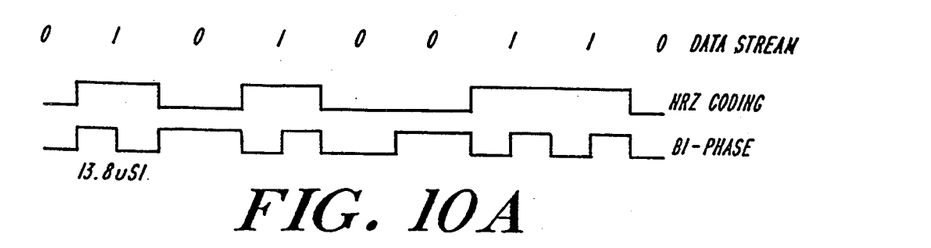
FIG. 10A is a bit map showing bi-phase encoding.

As mentioned above, FIG. 10A shows a series of bits in bi-phase encoding. In bi-phase encoding, there is always a transition at the beginning of each bit. If the data bit is a 0 there is no transition in the middle of the bit, whereas if the data bit is a 1 there is a transition in the middle of the bit. Bi-phase encoding is self clocking, and provides DC-free and band-limited transmission. Using bi-phase encoding in the EEG monitor of the present invention allows transformer and/or capacitive coupling and filtering of the data lines as the transformers and capacitors only pass AC signals.

Because the data coming into the data acquisition module 14 is entirely AC, transformers may be used to AC-couple into the data acquisition module 14. As shown in FIG. 4, a data receiver 116 translates the signals to TTL levels for the decoder 66. A full-wave bridge rectifier circuit 112 on the transformer outputs is used to extract power directly from the interface line.

The interface 80, 82 is implemented with programmable logic devices (PLD) that are mapped into the data address space of the integer digital signal processor 122. The programmable logic devices form a state machine running at 2.097152 MHz in the preferred embodiment. Using this technique, a phase locked loop for recovering the encoded clock and data is unnecessary.

Figure 10B:
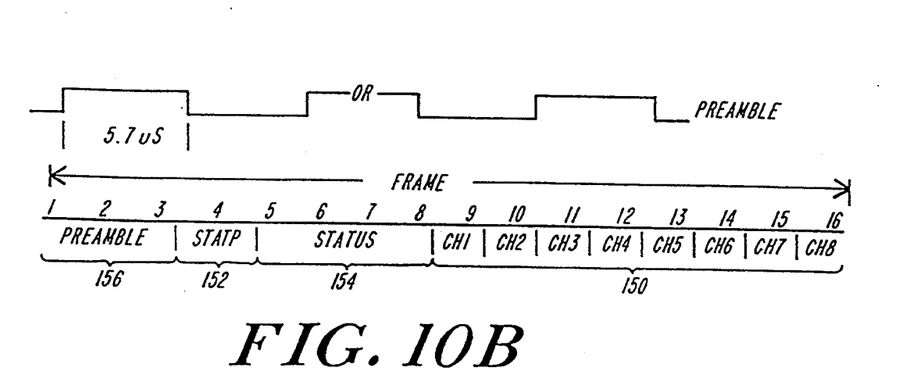
FIG. 10B is a bit map of the interface protocol used by the EEG monitor shown in FIG. 1.

FIG. 10b shows the protocol for the interface. In the preferred embodiment, up to 8 channels of EEG data may be carried by the interface. The EEG data bits 150 are multiplexed onto the data line along with a STATUS PRESENT bit 152 and 4 bits of status data 154. The bits are framed with a unique preamble 156 whose timing is a violation (i.e. there is no transition at the bit cell boundary or as an example the pulse is 3 half cells long, not 1 or 2 as specified in biphase rules of the bi-phase code interval). An interrupt to the integer digital signal processor 122 is generated at the end of each frame (in the preferred embodiment of full 16 bits) and is used as the main program timer for the integer digital signal processor. The timer internal to the processor provides a watchdog function for the interface.

Figure 10C:
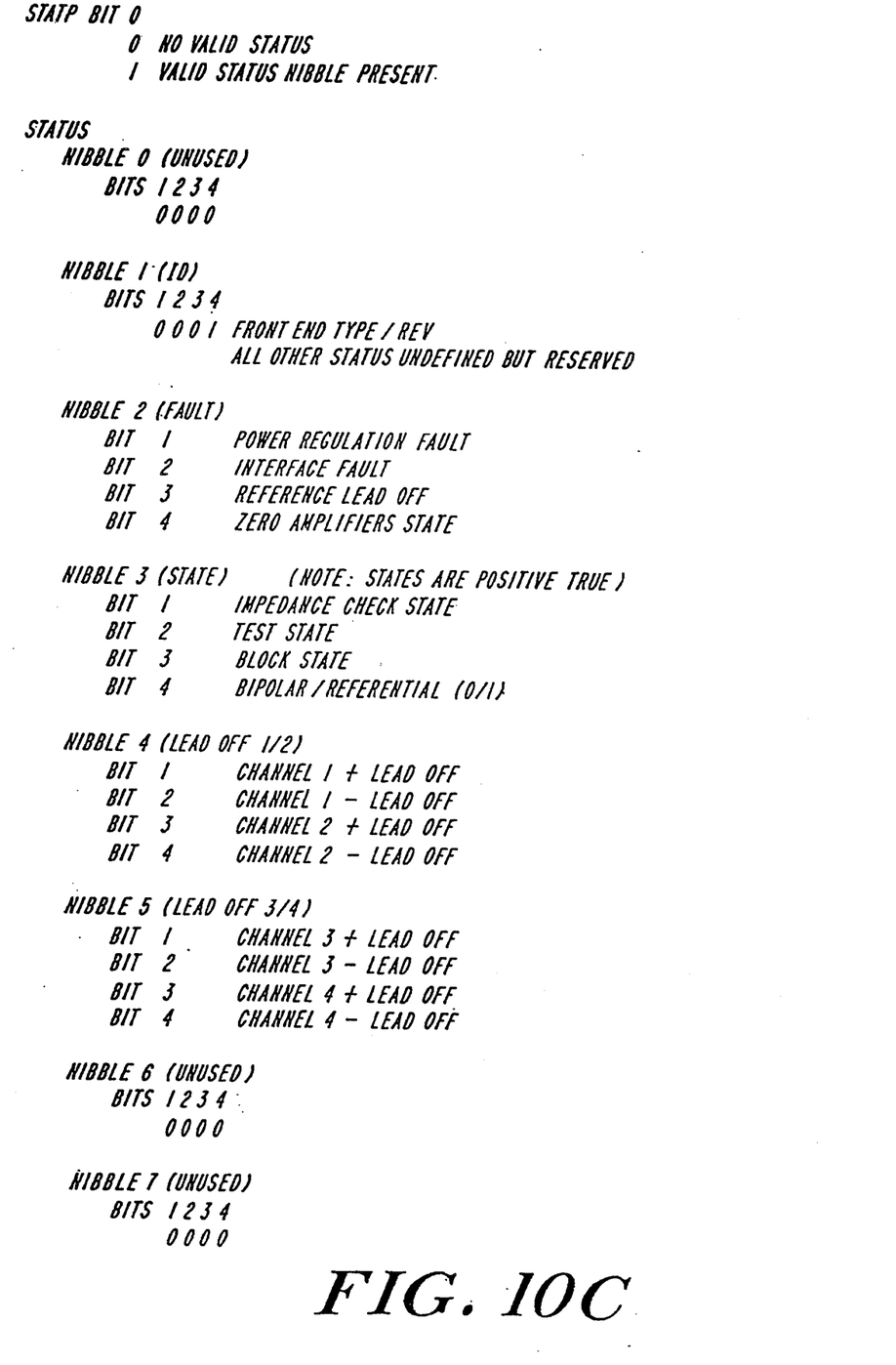
FIG. 10C is a chart of the status protocol used by the EEG monitor shown in FIG. 1.

Status nibbles are sent to the data processing module 12 only when requested by the host. Referring to FIG. 10C, the status protocol is shown. The STATUS PRESENT bit is normally set low. The bit is set high to indicate that a valid status message is coming. The 4 bit status nibbles are individually addressable.

Figure 10D:
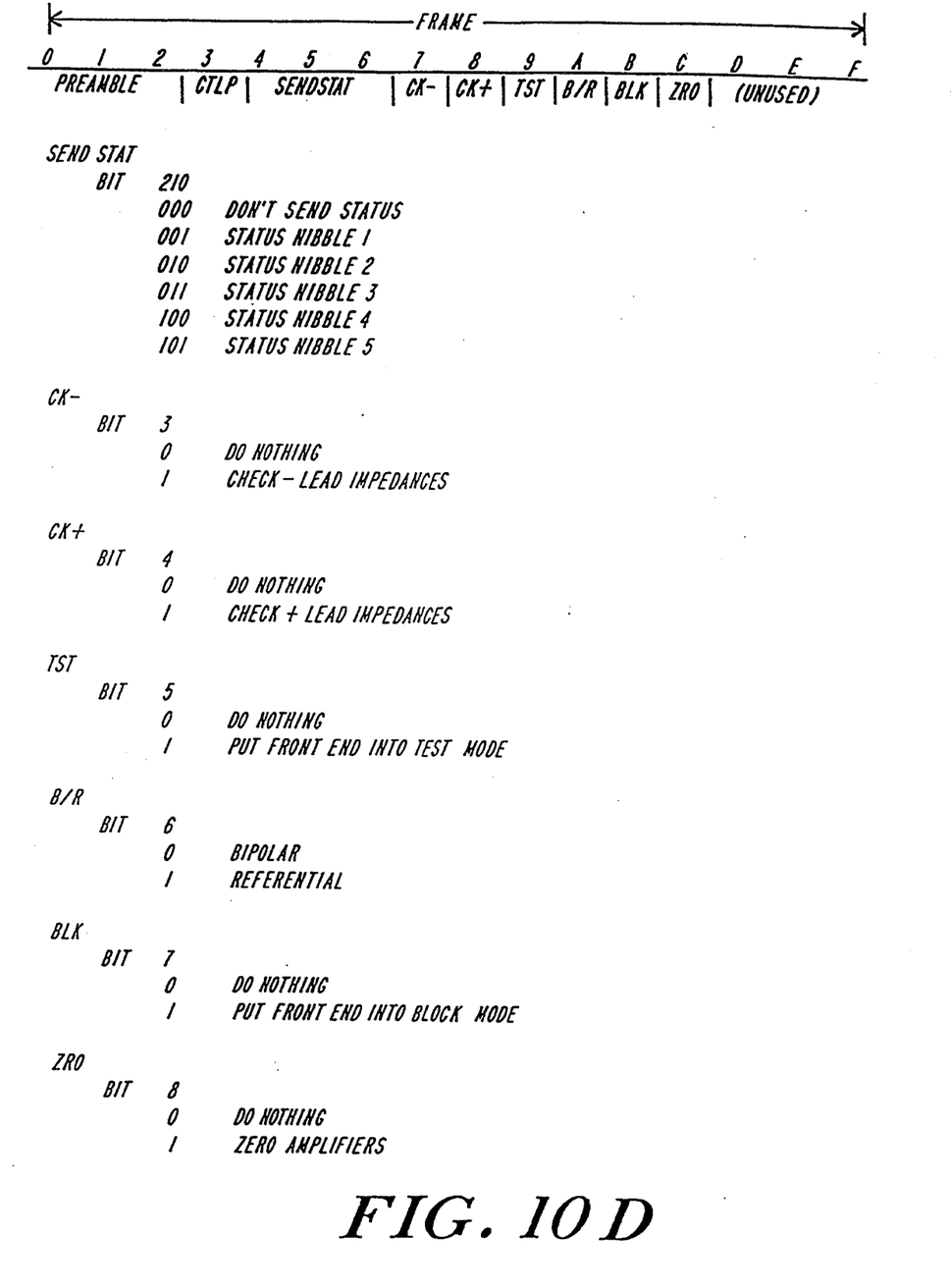
FIG. 10D is a chart of the control protocol used by the EEG monitor shown in FIG. 1.

Referring to FIG. 10D, the control protocol is shown. The control information is also framed with a preamble. Under normal conditions, no information is transmitted, and the line transmits all 0's. When a control message is to be sent by the host CPU 18 via the integer digital signal processor 122, the CONTROL PRESENT bit is set to 1 and the remaining bits in the frame contain the encoded control word. The control-in line 82 is driven by a power driver so that it may also provide the AC power for the data acquisition module 14.

Figure 11A:
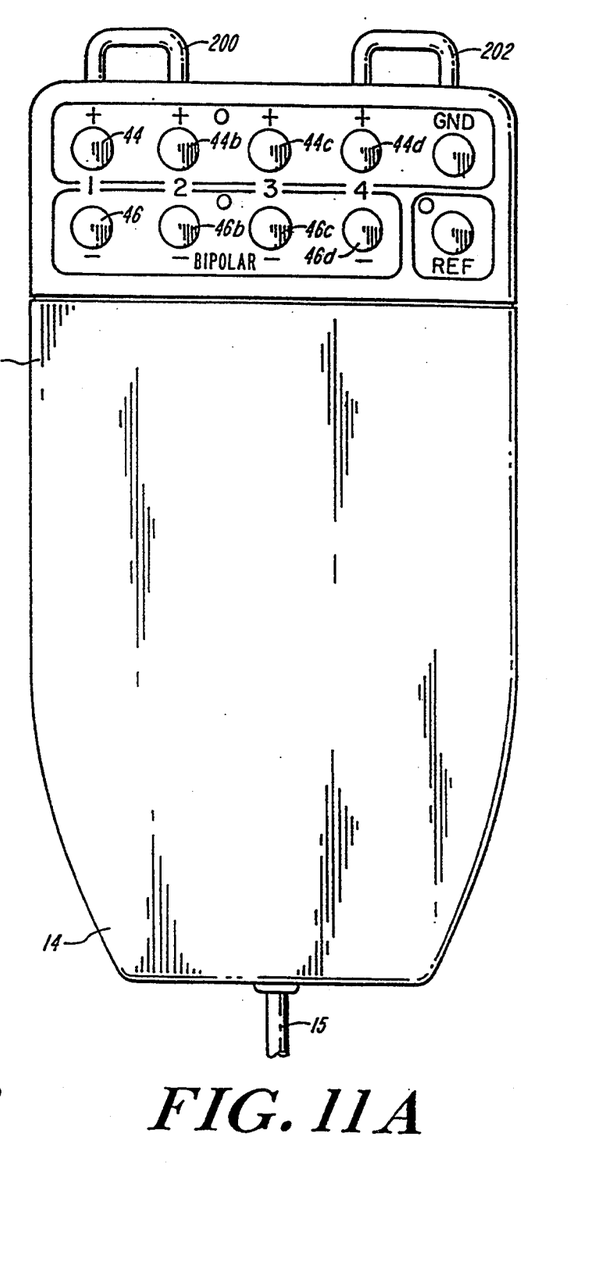
FIG. 11A is a front elevational view of the portable data acquisition module of the EEG monitor shown in FIG. 1.
Figure 11B:
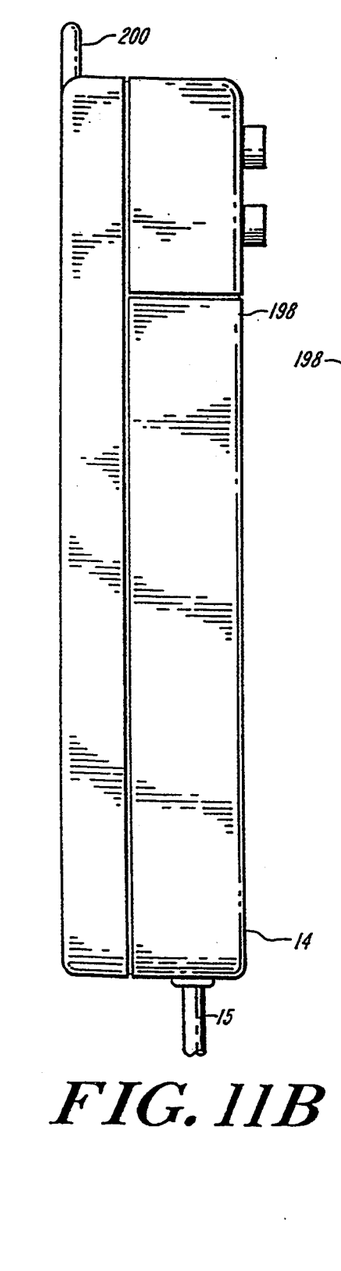
FIG. 11B is a side elevational view of the portable data acquisition module of the EEG monitor shown in FIG. 1.

Referring to FIGS. 11A and 11B, the portable data acquisition module 14 is contained in a small, custom-designed plastic case 198. The case has two large eyelets 200, 202 at the top to allow the user to use a strap to hang or pin the module 14. Patient electrode connection input jacks 44, 46, 44b, 46b, 44c, 46c, 44dd and 46d are standard 0.080 inch pin and are located on the top surface at one end of the case.

The data acquisition module 14 is connected to the data processing module 12 via thin, highly flexible cable 15. Cable 15 is strain-relieved and is permanently attached to the case 98. The cable 15 has two disconnection points. The cable is detachable at the processing module 12 and at a second disconnection point one foot from the data acquisition module 14. High-quality plastic Lemo connectors are used at the disconnection points in-line with the cable.

The case 198 is designed without ventilation holes in order to prevent damage from liquids which could be splashed while in use. Because of the use of low power circuitry, the surface of the case 198 will not exceed 50° C. while being covered with a bed pillow at 20° C. ambient temperature. The case 198 is made of a material that will enable it to survive a drop from up to 48 inches onto a concrete floor. The case 198 is electrically shielded both to prevent spurious emissions from data acquisition module 14 and to prevent externally caused interference with the data acquisition module 14 circuits.

While the foregoing invention has been described with reference to its preferred embodiments, it should be understood that various modifications and alterations will occur to those practiced in the art. Such modifications and alterations are intended to fall within the scope of the appended claims.

What is claimed is:

1. A monitor for receiving electrical signals from a living body and processing such signals to obtain information relating to a bodily function or organ, said monitor comprising
   a power supply located in a housing of said monitor;
   means for acquiring electrical signals through one or more electrodes connected to the body;
   means for transmitting both data and power over said same means for transmitting between said housing for said power supply and said means for acquiring electrical signals.

2. The monitor for receiving electrical signals from a living body of claim 1 wherein said means for transmitting both data and power comprises a single transmission line.

3. The monitor for receiving electrical signals from a living body of claim 1 wherein said means for transmitting is connected to a transformer which couples signals from a means for processing and said power supply to said means for acquiring electrical signals.

4. The monitor for receiving electrical signals from a living body of claim 3 further comprising:
   means for rectifying said coupled signals received by said means for acquiring electrical signals to produce a DC signal;
   means for linearly regulating said DC signal to provide power at appropriate voltage levels to said means for acquiring electrical signals.

5. A monitor for receiving electrical signals from a living body and processing such signals to obtain information relating to a bodily function or organ, said monitor comprising
   a power supply located in a housing of said monitor;
   means for acquiring electrical signals through one or more electrodes connected to the body;
   means for transmitting both biphase encoded data and power over said same means for transmitting between said housing for said power supply and said means for acquiring electrical signals.

* * * * *